United States Patent
Qiu et al.

(10) Patent No.: US 9,029,600 B2
(45) Date of Patent: May 12, 2015

(54) METHOD FOR PREPARING HIGH PURITY MONO-HYDROLYZED ACYL HALIDE COMPOUND

(75) Inventors: XiaoHua S. Qiu, Midland, MI (US); Steven D. Jons, Eden Prairie, MN (US); Joseph D. Koob, Jordan, MN (US); Martin H. Peery, Bloomington, MN (US); Steven Rosenberg, Shorewood, MN (US); Abhishek Roy, Edina, MN (US); Ian A. Tomlinson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/125,208

(22) PCT Filed: Sep. 14, 2012

(86) PCT No.: PCT/US2012/055269
§ 371 (c)(1),
(2), (4) Date: Dec. 10, 2013

(87) PCT Pub. No.: WO2013/048764
PCT Pub. Date: Apr. 4, 2013

(65) Prior Publication Data
US 2014/0206900 A1 Jul. 24, 2014

Related U.S. Application Data

(60) Provisional application No. 61/540,554, filed on Sep. 29, 2011.

(51) Int. Cl.
*C07C 51/58* (2006.01)
*C07C 51/62* (2006.01)
*C07C 53/42* (2006.01)
*C07F 9/11* (2006.01)

(52) U.S. Cl.
CPC ............... *C07C 51/58* (2013.01); *C07C 51/62* (2013.01)

(58) Field of Classification Search
CPC ........... C07C 51/58; C07C 51/62; C07F 9/09; C07F 9/11
USPC .................................. 562/495, 602; 558/208
See application file for complete search history.

(56) References Cited

U.S. PATENT DOCUMENTS

| | | | |
|---|---|---|---|
| 3,304,310 A | 2/1967 | Hari et al. |
| 3,686,116 A | 8/1972 | Andre Rio |
| 3,878,109 A | 4/1975 | Ikeda et al. |
| 4,259,183 A | 3/1981 | Cadotte |
| 4,277,344 A | 7/1981 | Cadotte |
| 4,529,646 A | 7/1985 | Sundet |
| 4,606,943 A | 8/1986 | Rak et al. |
| 4,626,468 A | 12/1986 | Sundet |
| 4,643,829 A | 2/1987 | Sundet |
| 4,719,062 A | 1/1988 | Sundet |
| 4,758,343 A | 7/1988 | Sasaki et al. |
| 4,761,234 A | 8/1988 | Uemura et al. |
| 4,783,346 A | 11/1988 | Sundet |
| 4,812,270 A | 3/1989 | Cadotte et al. |
| 4,830,885 A | 5/1989 | Tran et al. |
| 4,888,116 A | 12/1989 | Cadotte et al. |
| 4,948,507 A | 8/1990 | Tomaschke |
| 4,950,404 A | 8/1990 | Chau |
| 4,960,517 A | 10/1990 | Cadotte |
| 5,015,380 A | 5/1991 | Sundet |
| 5,015,382 A | 5/1991 | Sundet |
| 5,019,264 A | 5/1991 | Arthur |
| 5,051,178 A | 9/1991 | Uemura et al. |
| 5,160,619 A | 11/1992 | Yamaguchi et al. |
| 5,246,587 A | 9/1993 | Tomaschke |
| 5,254,261 A | 10/1993 | Tomaschke et al. |
| 5,290,452 A | 3/1994 | Schucker |
| 5,336,409 A | 8/1994 | Hachisuka et al. |
| 5,510,527 A | 4/1996 | Hachisuka et al. |
| 5,576,057 A | 11/1996 | Hirose et al. |
| 5,582,725 A | 12/1996 | McCray et al. |
| 5,593,588 A | 1/1997 | Kim et al. |
| 5,614,099 A | 3/1997 | Hirose et al. |
| 5,616,249 A | 4/1997 | Hodgdon |
| 5,693,227 A | 12/1997 | Costa |
| 5,733,602 A | 3/1998 | Hirose et al. |
| 5,736,371 A | 4/1998 | Samain et al. |
| 5,744,039 A | 4/1998 | Itoh et al. |
| 5,783,079 A | 7/1998 | Kumano et al. |
| 5,843,351 A | 12/1998 | Hirose et al. |
| 5,876,602 A | 3/1999 | Jons et al. |
| 5,989,426 A | 11/1999 | Hirose et al. |
| 6,024,873 A | 2/2000 | Hirose et al. |
| 6,086,764 A | 7/2000 | Linder et al. |

(Continued)

FOREIGN PATENT DOCUMENTS

| CN | 1035338 | 9/1989 |
|---|---|---|
| CN | 102219673 | 10/2011 |

(Continued)

OTHER PUBLICATIONS

Marvel, et al., Journal of Organic Chemistry, vol. 18, No. 12, (1953) 1664-1669.

(Continued)

*Primary Examiner* — Yong Chu
(74) *Attorney, Agent, or Firm* — Edward W. Black

(57) ABSTRACT

A method for preparing a high purity (e.g. greater than 70 wt. %) mono-hydrolyzed acyl halide compound as a precipitate from solution comprising the steps of preparing a solution comprising: i) at least 80 v/v % of a hydrocarbon solvent, ii) water at a molar concentration greater than its solubility limit within the solvent but less that its solubility limit in solution, iii) a tri-hydrocarbyl phosphate compound, and iv) a polyfunctional acyl halide compound at molar ratio to both water and the tri-hydrocarbyl phosphate compound of at least 1:1.

15 Claims, No Drawings

(56) References Cited

U.S. PATENT DOCUMENTS

| | | | |
|---|---|---|---|
| 6,162,358 | A | 12/2000 | Li et al. |
| 6,280,853 | B1 | 8/2001 | Mickols |
| 6,337,018 | B1 | 1/2002 | Mickols |
| 6,406,626 | B1 | 6/2002 | Murakami et al. |
| 6,464,873 | B1 | 10/2002 | Tomaschke |
| 6,521,130 | B1 | 2/2003 | Kono et al. |
| 6,562,266 | B2 | 5/2003 | Mickols |
| 6,723,241 | B2 | 4/2004 | Mickols |
| 6,723,422 | B1 | 4/2004 | Hirose et al. |
| 6,878,278 | B2 | 4/2005 | Mickols |
| 7,279,097 | B2 | 10/2007 | Tomioka et al. |
| 7,806,275 | B2 | 10/2010 | Murphy et al. |
| 7,815,987 | B2 | 10/2010 | Mickols et al. |
| 8,147,735 | B2 | 4/2012 | Buschmann |
| 8,177,978 | B2 | 5/2012 | Kurth et al. |
| 2012/0261332 | A1 | 10/2012 | Takagi et al. |
| 2012/0305473 | A1 | 12/2012 | Ogawa et al. |
| 2013/0089727 | A1 | 4/2013 | Nilsen et al. |
| 2013/0126419 | A1 | 5/2013 | Ogawa et al. |
| 2013/0256215 | A1 | 10/2013 | Nakatsuji et al. |

FOREIGN PATENT DOCUMENTS

| | | |
|---|---|---|
| JP | 53146275 | 12/1978 |
| WO | 2012102942 | 1/2012 |
| WO | 2012102943 | 8/2012 |
| WO | 2012102944 | 8/2012 |
| WO | 2013032586 | 3/2013 |
| WO | 2013048762 | 4/2013 |
| WO | 2013048763 | 4/2013 |
| WO | 2013048765 | 4/2013 |
| WO | 2013103666 | 4/2013 |
| WO | 2014014662 | 1/2014 |
| WO | 2014014663 | 1/2014 |
| WO | 2014014664 | 1/2014 |
| WO | 2014014666 | 1/2014 |
| WO | 2014014668 | 1/2014 |
| WO | 2014014669 | 1/2014 |

OTHER PUBLICATIONS

Dow Global Technologies LLC, PCT/US13/020072, filed Jan. 3, 2013.

Li et al, Polyamide thin fim composite membranes prepared from isomeric biphenyl tetraacyl chloride and m-phenylenediamine, Jornal of Membrane Science 315, (2008)20-27.

U.S. Appl. No. 61/818,934, filed May 3, 2013 by Mou Paul.

METHOD FOR PREPARING HIGH PURITY MONO-HYDROLYZED ACYL HALIDE COMPOUND

CROSS REFERENCE TO RELATED APPLICATIONS

This application is a 371 of PCT/US2012/055269 filed Sep. 14, 2012, which claims the benefit of U.S. Provisional Application No. 61/540,554 filed on Sep. 29, 2011.

FIELD OF THE INVENTION

The present invention is directed toward methods for preparing high purity mono-hydrolyzed acyl halide compounds as precipitates.

BACKGROUND

Known techniques for preparing mono-hydrolyzed acyl-halide compounds via hydrolysis of polyfunctional acyl-halide compounds offer low yields, e.g. see U.S. Pat. No. 3,304,310. Techniques for producing higher yields of such mono-hydrolyzed acyl-halide compounds are desired.

BRIEF SUMMARY OF THE INVENTION

The present invention includes methods for preparing a mono-hydrolyzed acyl halide compound as a precipitate from solution comprising the steps of preparing a solution comprising:
 i) at least 80 v/v % of a hydrocarbon solvent,
 ii) water at a molar concentration greater than its solubility limit within the solvent but less that its solubility limit in solution,
 iii) a tri-hydrocarbyl phosphate compound, and
 iv) a polyfunctional acyl halide compound at molar ratio to both water and the tri-hydrocarbyl phosphate compound of at least 1:1.

In preferred embodiments, the precipitate comprises at least 70 wt %, 80 wt % and in some embodiments at least 90 wt % of the mono-hydrolyzed acyl halide compound.

DETAILED DESCRIPTION OF THE INVENTION

The polyfunctional acyl halide compound(s) of the present invention includes an aliphatic or arene moiety including a plurality of acyl halide functional groups. In a preferred set of embodiments, the polyfunctional acyl halide compound and corresponding mono-hydrolyzed acyl halide compound have molecular weights less than 700, 600, 500, 400 or 300 Daltons. In another set of embodiments, the polyfunctional acyl halide compound and mono-hydrolyzed acyl halide compound comprises equal to or less than 30, 20, 15 or 12 carbon atoms, and preferably include more than 3 carbon atoms. In yet another set of embodiments, the polyfunctional acyl halide compound and mono-hydrolyzed acyl halide compound comprises from 4 to 12 carbon atoms. Non-limiting examples of polyfunctional acyl halide compounds based upon aliphatic moieties include: $C_4$ through $C_{12}$ alkanes (e.g. succinyl, glutaroyl, adipoyl, heptanedioyl, octanedioyl, nonanedioyl, decanedioyl, undecanedioyl and dodecanedioyl di and tri chloride), cycloalkanes (e.g. cyclopropane tri carboxylic acid chloride, cyclobutane tetra carboxylic acid chloride, cyclopentane tri carboxylic acid chloride, cyclopentane tetra carboxylic acid chloride, cyclohexane tri carboxylic acid chloride, tetrahydrofuran tetra carboxylic acid chloride, cyclopentane dicarboxylic acid chloride, cyclobutane dicarboxylic acid chloride, cyclohexane dicarboxylic acid chloride, tetrahydrofuran dicarboxylic acid chloride, cyclohexane-1,3,5-tricarbonyl trichloride, and decahydronaphthalene-2,6-dicarbonyl dichloride. Non-limiting examples of polyfunctional acyl halide compounds based upon arene moieties include: terephthaloyl dichloride, isophthalic acid dichloride, benzene-1,3,5-tricarbonyl trichloride and naphthalene-2,6-dicarbonyl dichloride. Additional examples of polyfunctional acyl halide compounds include branched analogs of the preceding compounds along analogs including additional acyl halide functional groups. Examples of preferred polyfunctional acyl halide compounds include the mono-hydrolyzed analog of the preceding compounds.

The selection of hydrocarbon solvent is not particularly limited and combinations of multiple solvents may be used. The solvent is preferably a liquid at 20° C. (101 kPa). The solvent preferably has a water solubility of less than 800 ppm (and more preferably less than 500, 400, 300, or 200, or in some embodiments, less than 150 ppm). As used herein, the term "water solubility" refers to the concentration of water that is soluble in a chosen hydrocarbon solvent measured at 20° C. (101 kPa) as measured by ASTM D4928-11. Non-limiting examples of applicable hydrocarbon solvents include: paraffins (e.g. hexane, cyclohexane, heptane, octane, dodecane), isoparaffins (e.g. ISOPAR™ series), aromatics (e.g. benzene, 1,3,5-trimethylbenzene, toluene), halogenated hydrocarbons (e.g. FREON™ series, chlorobenzene, di- and trichlorobenzene), and mixtures there of.

Tri-hydrocarbyl phosphate compounds applicable in the present invention include those represented by Formula (I):

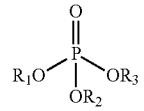

Formula (I)

wherein "P" is phosphorous, "O" is oxygen and $R_1$, $R_2$ and $R_3$ are independently selected from hydrogen and hydrocarbyl groups comprising from 1 to 10 carbon atoms, with the proviso that no more than one of $R_1$, $R_2$ and $R_3$ are hydrogen. $R_1$, $R_2$ and $R_3$ are preferably independently selected from aliphatic and arene groups. Applicable aliphatic groups include both branched and unbranched species, e.g. methyl, ethyl, propyl, isopropyl, butyl, isobutyl, pentyl, 2-pentyl, 3-pentyl, cyclopentyl, hexyl, 2-ethylhexyl, cyclohexyl, etc.; however, alkyl groups having from 3 to 10 carbon atoms are preferred. Applicable arene groups include phenyl and naphthyl groups. Specific examples of tri-hydrocarbyl phosphate compounds include: tripropyl phosphate, tributyl phosphate, tripentyl phosphate, trihexyl phosphate, triphenyl phosphate, propyl diphenyl phosphate, dibutyl phenyl phosphate, butyl diethyl phosphate, dibutyl hydrogen phosphate, butyl heptyl hydrogen phosphate and butyl heptyl hexyl phosphate.

The aforementioned constituents may be initially combined and mixed within a reaction vessel at room temperature. While the order of addition is not particularly limited, in preferred embodiments the polyfunctional acyl halide compound is contacted with the tri-hydrocarbyl phosphate compound prior to contact with water.

The aforementioned constituents are combined to form a solution comprising at least 80 v/v % hydrocarbon solvent, and in some embodiments at least 90 v/v %, 92 v/v % or 95 v/v % hydrocarbon solvent along with: i) water at a molar concentration greater than its solubility limit within the solvent but less that its solubility limit with the solution, ii) a tri-hydrocarbyl phosphate compound as previously described, and iii) a polyfunctional acyl halide compound at molar ratio to both water and the tri-hydrocarbyl phosphate compound of at least 1:1.

The invention includes both continuous processes where the constituents are maintained within certain concentrations or ratios, and batch processes which operate until the concentrations of the constituents fall outside of the ranges previously described. For example, in one embodiment, at least one and preferably both the polyfunctional acyl halide compound and water are continuously added to the solution and the precipitate is continuously formed. For example, the concentration of the polyfunctional acyl halide compound may be maintained in the solution at a molar ratio greater than 1:1 with water and at least 2:1 with the tri-hydrocarbyl phosphate compound. In other embodiment of a continuous process, the concentration of water is maintained in the solution at a concentration greater than its solubility limit within the solvent but less that its solubility limit in solution. In a preferred embodiment, the concentration of water is maintained in a range from 100 ppm to 1 weight percent of water. In another embodiment, the concentration of the polyfunctional acyl halide compound in solution is maintained in a range from 0.1 to 20 weight percent.

In preferred embodiments, the mono-hydrolyzed analog of the polyfunctional acyl halide compound comprises at least 70 wt. % of the precipitate formed in the solution. In other embodiments, at least 80 wt. %, 90 wt %, 92 wt. %, 95 wt % or even at least 98 wt % of the precipitate is the mono-hydrolyzed analog of the polyfunctional acyl halide compound. Representative reaction pathways are illustrated below.

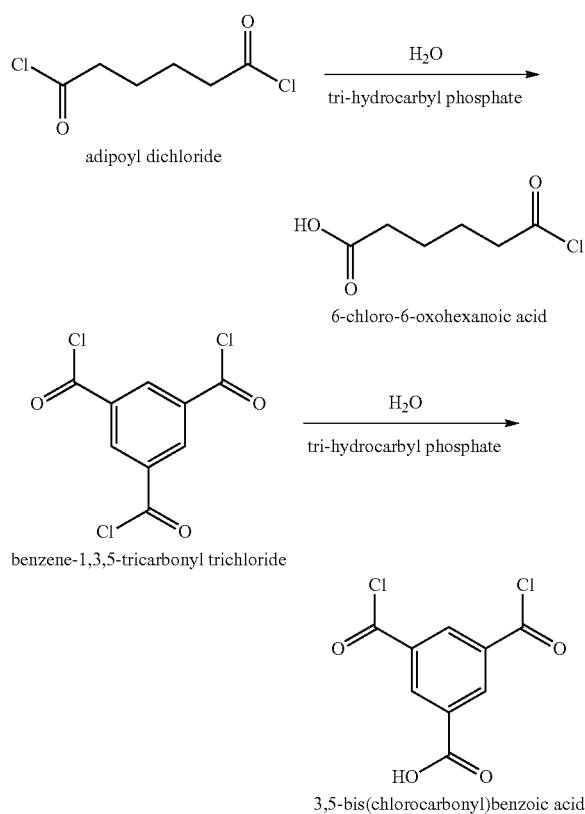

adipoyl dichloride 6-chloro-6-oxohexanoic acid benzene-1,3,5-tricarbonyl trichloride 3,5-bis(chlorocarbonyl)benzoic acid The mono-hydrolyzed acyl halide compound has a solubility limit of less than 1 wt. % in the hydrocarbon solvent and in some embodiments less than 0.1 wt %, 0.05 wt %, 0.02 wt % or in still others, less than even 0.01 wt %. While not wishing to be bound by theory, it is believed that the subject class of tri-hydrocarbyl phosphates increases the solubility of water within the hydrocarbon solvent and facilitates hydrolysis of the polyfunctional acyl halide compound. Surprisingly, the reaction is highly selective toward the mono-hydrolyzed species. The precipitate can be easily recovered and optionally washed, e.g. with solvent and conveniently stored. The mono-hydrolyzed acyl halide compound has a variety of uses including in the preparation of polyamides.

Many embodiments of the invention have been described and in some instances certain embodiments, selections, ranges, constituents, or other features have been characterized as being "preferred." Characterizations of "preferred" features should in no way be interpreted as deeming such features as being required, essential or critical to the invention. For purposes of this description, the terms "acyl halide" and "acid halide" have the same meaning. While much of the description has focused upon acyl chlorides, non-chloride halides are also included. The term "solubility limit" refers to the point at which no additional amount of a constituent, (e.g. water, mono-hydrolyzed acyl halide compound, polyfunctional acyl halide compound) is miscible or dissolvable with the hydrocarbon solvent or solution, as measured at 20° C. and 101 kPa. Unless otherwise stated, all solubility related parameters are determined at 20° C. and 101 kPa.

EXAMPLES

A 100 mL starter solution was made by combining an acid chloride, additive, solvent and water according to the formulation outlined for each entry in the table below. The starter solution was allowed to stir for 14-20 hours after which time an additional 1 g of the acid chloride and 0.0076 mL of water was added. The solution was allowed to stir for 1-2 hours and an additional 0.0076 mL of water was added. This was repeated until a total of 4 additions of 0.0076 mL of water were added to the starter solution. The resulting white precipitate was collected using filter paper and washed repeatedly with fresh solvent. The precipitate was redissolved in Isopar L by adding 0.165 wt % TBP and the product selectivity was determined using $^1$H NMR. The observed product selectivity is summarized in Table 1 below.

TABLE 1

| Example No. | Acid Chloride type | wt % | Additive type | wt % | Solvent | Water (ppm) | Product Selectivity (%) |
|---|---|---|---|---|---|---|---|
| 1-1 | TMC | 1.2 | TBP | 0.56 | Isopar L | 100 | 99 |
| 1-2 | IPC | 1.0 | TBP | 0.48 | Isopar L | 20 | 100 |
| 1-3 | TMC | 2.0 | TEP | 0.65 | Isopar L | 20 | 100 |
| 1-4 | TMC | 3.9 | TEHP | 1.30 | Isopar L | 20 | 94.8 |
| 1-5 | TMC | 2.0 | TBP | 0.65 | 90/10 Isopar L/toluene | 20 | 100 |

"TMC" is trimesoyl chloride. "IPC" is isophthaloyl chloride. "TBP" is tributyl phosphate. "TEP" is triethyl phosphate. "TEHP" is tris(2-ethyl hexyl) phosphate.

The invention claimed is:
1. A method for preparing a mono-hydrolyzed acyl halide compound as a precipitate from solution comprising the step of preparing a solution comprising:

i) at least 80 v/v % of a hydrocarbon solvent having a water solubility of less than 800 ppm,
ii) water at a molar concentration greater than its solubility limit within the solvent but less that its solubility limit in solution,
iii) a tri-hydrocarbyl phosphate compound, and
iv) a polyfunctional acyl halide compound at molar ratio to both water and the tri-hydrocarbyl phosphate compound of at least 1:1.

2. The method of claim 1 wherein the precipitate comprises at least 70 wt % of the mono-hydrolyzed acyl halide compound.

3. The method of claim 1 wherein the precipitate comprises at least 90 wt % of the mono-hydrolyzed acyl halide compound.

4. The method of claim 1 wherein at least one of the polyfunctional acyl halide compound or water are continuously added to the solution.

5. The method of claim 1 wherein both the polyfunctional acyl halide compound and water are continuously added to the solution.

6. The method of claim 1 wherein the concentration of the polyfunctional acyl halide compound is maintained in the solution at a molar ratio greater than 1:1 with water and at least 2:1 with the tri-hydrocarbyl phosphate compound.

7. The method of claim 1 wherein the concentration of water is maintained in the solution at a concentration greater than its solubility limit within the solvent but less that its solubility limit in solution.

8. The method of claim 1 wherein the solution comprises from 100 ppm to 1 weight percent of water.

9. The method of claim 1 wherein the solution comprises from 0.1 to 20 weight percent of the polyfunctional acyl halide compound.

10. The method of claim 1 wherein the polyfunctional acyl halide compound and mono-hydrolyzed acyl halide compound both have a molecule weight less than 300 Daltons.

11. The method of claim 1 wherein the polyfunctional acyl halide compound and mono-hydrolyzed acyl halide compound both comprise equal to or less than 30 carbon atoms.

12. The method of claim 1 wherein the polyfunctional acyl halide compound and mono-hydrolyzed acyl halide compound both comprise from 4 to 12 carbon atoms.

13. The method of claim 1 wherein the polyfunctional acyl halide compound comprises a carbon containing moiety selected from: an arene group substituted with a plurality of acyl halide functional groups; and the mono-hydrolyzed acyl halide compound comprises an arene group substituted with at least one acyl halide functional group and a carboxylic acid functional group.

14. The method of claim 1 wherein the tri-hydrocarbyl compound is represented by:

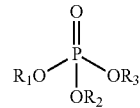

wherein $R_1$, $R_2$ and $R_3$ are independently selected from hydrogen and hydrocarbyl groups comprising from 1 to 10 carbon atoms, with the proviso that no more than one of $R_1$, $R_2$ and $R_3$ are hydrogen.

15. The method of claim 13 wherein $R_1$, $R_2$ and $R_3$ are independently selected from: aliphatic and arene groups.

* * * * *